US008918462B2

(12) United States Patent
McCallie, Jr. et al.

(10) Patent No.: US 8,918,462 B2
(45) Date of Patent: Dec. 23, 2014

(54) USING USER-ATTRIBUTE ONTOLOGIES TO CALCULATE USER-ANONYMITY DEGREES

(75) Inventors: David P. McCallie, Jr., Stilwell, KS (US); Margaret Cushing Kolm, Kansas City, MO (US); Christopher S. Finn, Liberty, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 400 days.

(21) Appl. No.: 12/986,285

(22) Filed: Jan. 7, 2011

(65) Prior Publication Data

US 2011/0173261 A1     Jul. 14, 2011

Related U.S. Application Data

(60) Provisional application No. 61/293,380, filed on Jan. 8, 2010.

(51) Int. Cl.
| | |
|---|---|
| *G06F 15/16* | (2006.01) |
| *G06F 21/62* | (2013.01) |
| *G06Q 50/24* | (2012.01) |
| *G06F 19/00* | (2011.01) |
| *H04L 29/06* | (2006.01) |
| *G06F 17/00* | (2006.01) |
| *G06Q 50/00* | (2012.01) |
| *G06Q 20/00* | (2012.01) |
| *H04L 29/08* | (2006.01) |

(52) U.S. Cl.
CPC ............ *G06F 21/6245* (2013.01); *G06Q 50/24* (2013.01); *G06F 19/322* (2013.01); *H04L 63/0407* (2013.01); *H04L 67/12* (2013.01)
USPC ...................... 709/204; 726/1; 705/3; 705/74

(58) Field of Classification Search
None
See application file for complete search history.

(56) References Cited

U.S. PATENT DOCUMENTS

| | | | |
|---|---|---|---|
| 7,269,578 B2 * | 9/2007 | Sweeney | .......................... 705/74 |
| 7,761,480 B2 * | 7/2010 | Toledano et al. | ............. 707/804 |
| 7,827,234 B2 * | 11/2010 | Eisenberger et al. | .......... 709/203 |
| 2009/0254971 A1 * | 10/2009 | Herz et al. | ......................... 726/1 |

* cited by examiner

*Primary Examiner* — Wen-Tai Lin
(74) *Attorney, Agent, or Firm* — Shook, Hardy & Bacon L.L.P.

(57) ABSTRACT

Computerized methods and systems for using user-attribute ontologies to calculate anonymity levels are provided. A semi-automated mechanism permits selective and optionally progressive exposure of demographic and clinical information to other members of a medical social network group that a member has joined. When a user decides to join a medical social network group (which may be based upon system suggestion or initiated of the user's own accord), he or she selects or creates a profile that has a statistically validated degree of anonymity, ranging from fully anonymous to fully transparent. Based upon a user's elected level of exposure, only certain data is exposed to the rest of the group's membership. Thus, the user is permitted to personally balance the tension between exposing a level of information that may render him or her personally identifiable and exposing enough information to obtain meaningful advice and/or camaraderie.

18 Claims, 5 Drawing Sheets

USING USER-ATTRIBUTE ONTOLOGIES TO CALCULATE USER-ANONYMITY DEGREES

BACKGROUND

Health record banks and/or electronic health records or other collections of medical data over which a subject patient has at least partial control over exposure thereof, often include large membership populations and contain detailed demographic and health information about their members. A core motivating philosophy of these systems is that each member has strict control over the privacy of at least portions of his or her own data and must trust the system to respect that privacy.

Members of these types of systems often wish to participate in medical social network groups, to share insights into their illnesses, to learn about how others that are similarly situated have managed, or to discuss treatment options, and the like. However, members still desire to protect their privacy, at least until they reach a certain level of trust with other members of the medical social network groups.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter Embodiments of the present invention relate to providing users with an indication of how anonymous they can be with respect to a medical social network group if they elect to expose certain information (e.g., values of user-attributes) about themselves to the group. In other words, embodiments of the present invention relate to using user-attributes having associated user-attribute ontologies to calculate degrees of user-anonymity that are conditioned on exposure of attribute values associated with various user-attributes to members of a medical social network group. Embodiments hereof utilize statistical masking methodologies, and take advantage of ontologies associated with various user-attributes that are in some way related to user demographics, medical conditions, medical diagnoses, or the like, to blur facts about users and calculate degrees of user-anonymity. Users may then utilize the calculated degrees of user-anonymity to aid them in deciding whether they wish to join a particular medical social network group and/or how much information they would like to expose to members of a particular medical social network group.

Accordingly, in one embodiment, the present invention is directed to one or more computer-readable storage media having computer-executable instructions embodied thereon for performing a method, in a clinical computing environment, for using user-attribute ontologies to calculate user-anonymity degrees. The method includes receiving an indication that a user desires to join a medical social network group having a plurality of members and receiving a plurality of attribute values, each attribute value being associated with a user-attribute. The method further includes calculating a degree of user-anonymity conditioned on exposure of at least one subset of the plurality of attribute values to members of the medical social network group and presenting an indication of the calculated degree of user-anonymity and an identity of each of the plurality of attribute values included in the at least one subset. In embodiments, at least a first and a second of the plurality of attribute values are associated with a common user-attribute, the common user-attribute including a multi-level user-attribute ontology related thereto, and each of the first and second of the plurality of attribute values is associated with a different level of the multi-level user-attribute ontology.

In another embodiment, the present invention is directed to a method, in a clinical computing environment, for providing medical social network group suggestions having anonymity degrees calculated, at least in part, using user-attribute ontologies. The method includes extracting or deriving a plurality of attribute values from a health record of a user, each attribute value being associated with a user-attribute. The method further includes receiving group-member attribute values for a plurality of members of a medical social network group, the group-member attribute values being associated with a common user-attribute associated with the plurality of attribute values, and calculating a degree of user-anonymity as it relates to the received group-member attribute values, the degree of user-anonymity being conditioned on exposure of at least one subset of the plurality of attribute values. Still further, the method includes presenting a suggestion that the user join the medical social network group and the calculated degree of user-anonymity upon determining that the calculated degree of user-anonymity meets or exceeds a threshold degree of user-anonymity. In embodiments, a first and a second of the plurality of attribute values are associated with the common user-attribute, the common user-attribute including a multi-level user-attribute ontology related thereto.

In yet another embodiment, the present invention is directed to one or more computer-readable storage media having computer-executable instructions embodied thereon for performing a method, in a clinical computing environment, for using user-attribute ontologies to calculate user-anonymity degrees. The method includes receiving an indication that a user desires to join a medical social network group having a plurality of members and receiving a plurality of attribute values, each attribute value being associated with a user-attribute. A first and a second of the plurality of attribute values are associated with a first common user-attribute, and the first common user-attribute includes a first multi-level user-attribute ontology related thereto. Each of the first and second of the plurality of attribute values is associated with a different level of the first multi-level user-attribute ontology. A third and a fourth of the plurality of attribute values are associated with a second common user-attribute, the second common user-attribute including a second multi-level user-attribute ontology related thereto, and each of the third and fourth of the plurality of attribute values is associated with a different level of the second multi-level user-attribute ontology. The method further includes calculating a plurality of degrees of user-anonymity conditioned on exposure of varying subsets of the plurality of attribute values. A first subset of the plurality of attribute values contains at least one of the first and second of the plurality of attribute values and one of the third and fourth of the plurality of attribute values. Still further, the method includes presenting an indication of the calculated degrees of user-anonymity and an identity of each of the plurality of attribute values included in the associated subset.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide users with an indication of how anonymous they can be with respect to a medical social network group if they elect to expose certain information (e.g., values of user-attributes) about themselves to the group. That is, embodiments of the present invention provide methods for using user-attributes having associated user-attribute ontologies to calculate degrees of user-anonymity that are conditioned on exposure of attribute values associated with various user-attributes to members of a medical social network group. Embodiments hereof utilize statistical masking by a process of ontologic blurring that takes advantage of ontologies associated with various user-attributes that are in some way related to user demographics, medical conditions, medical diagnoses, treatments, or the like, to calculate degrees of user-anonymity. Users may then utilize the calculated degrees of user-anonymity to aid them in deciding whether they wish to join a particular medical social network group and/or how much information they would like to expose to members of a particular medical social network group. An exemplary operating environment for embodiments of the present invention is described below.

Figure 1:
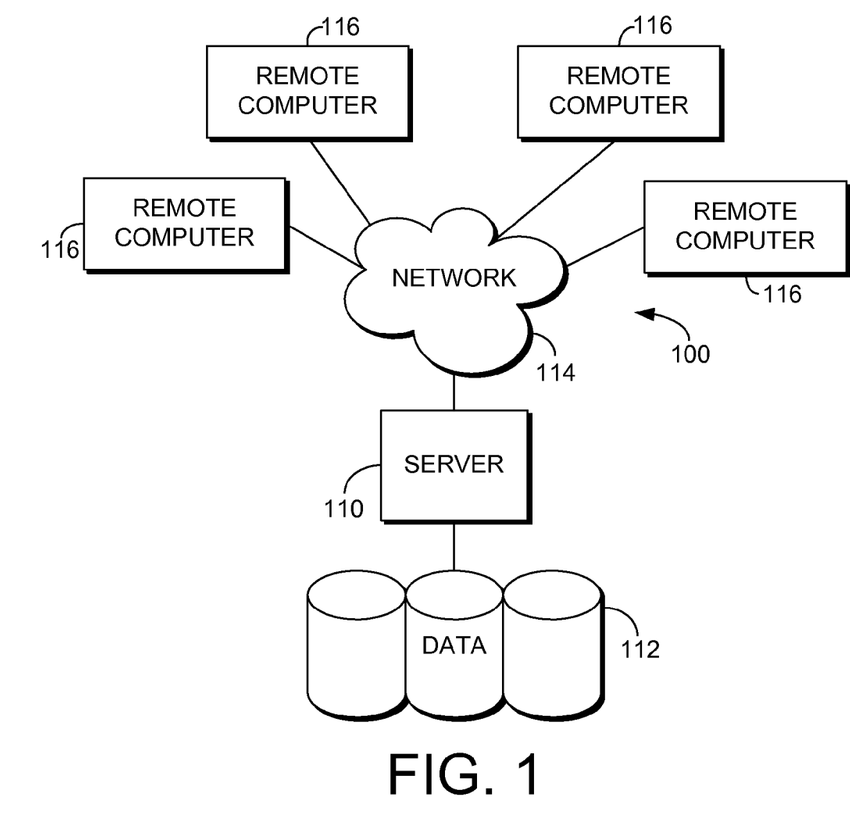
FIG. 1 is a block diagram of an exemplary computing environment suitable for use in implementing embodiments of the present invention.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of embodiments of the invention. Neither should the medical information computing system environment 100 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, mobile computing devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 110. Components of the server 110 may include, without limitation, a processing unit, internal system memory, and a suitable system bus for coupling various system components, including database cluster 112, with the server 110. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 110 typically includes, or has access to, a variety of computer-readable media, for instance, database cluster 112. Computer-readable media can be any available media that may be accessed by server 110, and includes volatile and nonvolatile media, as well as removable and non-removable media. By way of example, and not limitation, computer readable media may comprise computer-readable storage media. Computer-readable storage media may include, without limitation, volatile and nonvolatile media, as well as removable and non-removable media implemented in any method or technology for storage of information, such as computer-readable instructions, data structures, program modules, or other data. In this regard, computer-readable storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 110. Combinations of any of the above also may be included within the scope of computer-readable media.

The computer-readable storage media discussed above and illustrated in FIG. 1, including database cluster 112, provide storage of computer-readable instructions, data structures, program modules, and other data for the server 110.

The server 110 may operate in a computer network 114 using logical connections to one or more remote computers 116. The remote computers 116 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 116 may also be physically located in non-traditional medical care environments so that the entire health care community may be capable of integration on the network. The remote computers 116 may be personal computers, servers, routers, network PCs, peer devices, wireless computing devices, mobile computing devices, other common network nodes, or the like, and may include some or all of the elements described above in relation to the server 110. The devices can be personal digital assistants or other like devices.

Exemplary computer networks 114 may include, without limitation, local area networks (LANs) and/or wide area networks (WANs). Such networking environments are commonplace in offices, enterprise-wide computer networks, intranets, and the Internet. When utilized in a WAN networking environment, the server 110 may include a modem or other means for establishing communications over the WAN, such as the Internet. In a networked environment, program modules or portions thereof may be stored in the server 110, in the database cluster 112, or on any of the remote computers 116. For example, and not by way of limitation, various application programs may reside on the memory associated with any one or more of the remote computers 116. It will be appreciated by those of ordinary skill in the art that the network connections shown are exemplary and other means of establishing a communications link between the computers (e.g., server 110 and remote computers 116) may be utilized.

In operation, a user may enter commands and information into the server 110 or convey the commands and information to the server 110 via one or more of the remote computers 116 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 110. In addition to a monitor, the server 110 and/or remote computers 116 may include other peripheral output devices, such as speakers and a printer.

Although many other internal components of the server 110 and the remote computers 116 are not shown, those of ordinary skill in the art will appreciate that such components and their interconnection are well known. Accordingly, additional details concerning the internal construction of the server 110 and the remote computers 116 are not further disclosed herein.

Although methods and systems of embodiments of the present invention are described as being implemented in a WINDOWS operating system, operating in conjunction with an Internet-based system, one of ordinary skill in the art will recognize that the described methods can be implemented in any system supporting the receipt and processing of medically-related user-attributes and their associated values. In particular, the described methods can be implemented in any system supporting the receipt, extraction and derivation of information contained in electronic health records of a user. As contemplated by the language above, the methods of embodiments of the present invention may also be implemented on a stand-alone desktop, personal computer, mobile computing device, or any other computing device used in a healthcare environment, home-computing environment, or any of a number of other locations.

Figure 2:
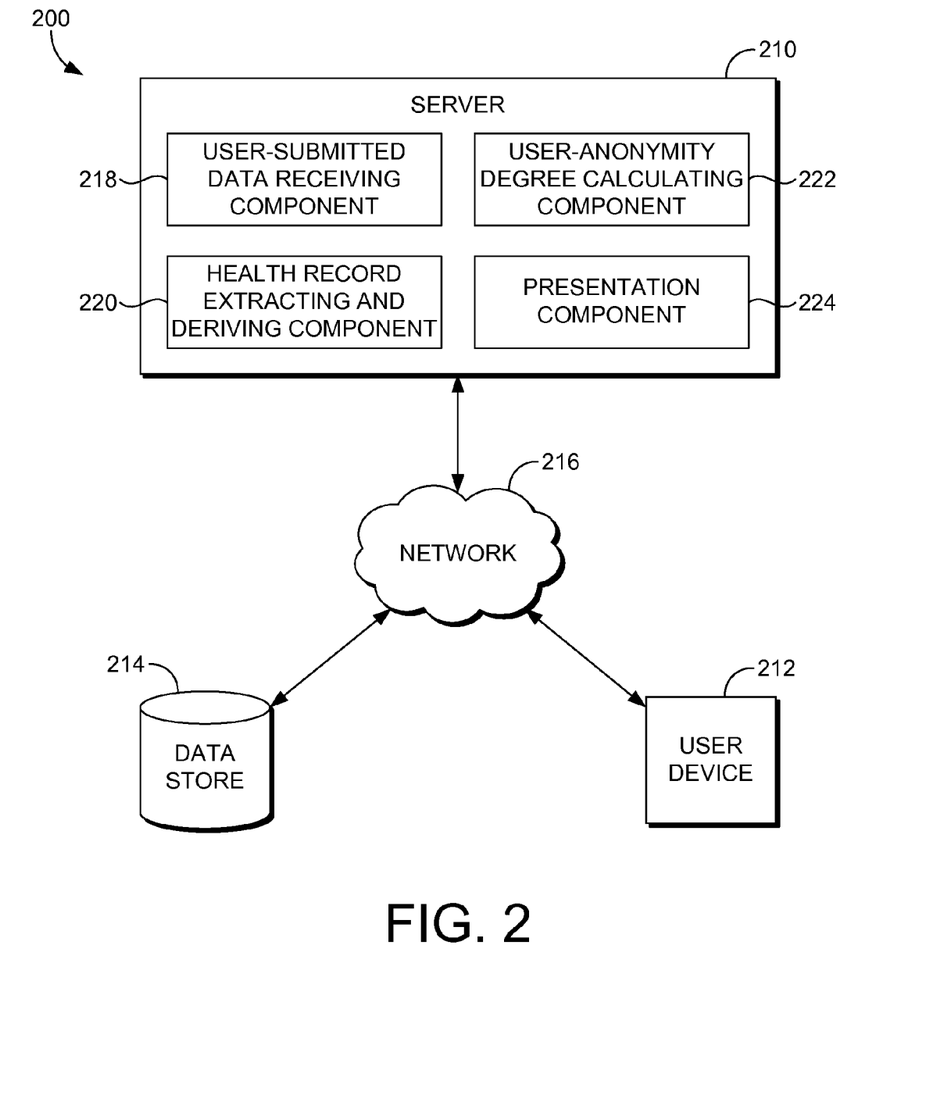
FIG. 2 is a block diagram of an exemplary computing system in which embodiments of the invention may be employed.

As previously mentioned, embodiments of the present invention relate to computerized methods for providing users with an indication of how anonymous they can be with respect to a medical social network group if they elect to expose certain information about themselves to the group. In other words, embodiments of the present invention relate to using user-attributes having associated user-attribute ontologies to calculate degrees of user-anonymity that are conditioned on exposure of attribute values associated with various user-attributes to members of a medical social network group. With reference to FIG. 2, an exemplary computing system suitable for implementing embodiments of the present invention is illustrated and designated generally as reference numeral 200. The system 200 includes a server 210, a user device 212, and a data store 214, all in communication with one another through a network 216. The network 216 may include, without limitation, one or more local area networks (LANs) and/or wide area networks (WANs). Such networking environments are commonplace in offices, enterprise-wide computer networks, intranets, and the Internet. Accordingly, the network 216 is not further described herein.

The data store 214 is configured to store information, for instance, associated with a plurality of patients' electronic medical records (EMRs), including electronic health records or other collections of medical data over which a subject patient has at least partial control of exposure. (The terms "individual," "person," and "patient" are used interchangeably herein and are not meant to limit the nature of the referenced individual in any way. Rather the methods and systems described herein are equally applicable, for instance, in a veterinary setting. Further, use of the term "patient" is not meant to imply any particular relationship between the individual and those inputting and/or individualizing any patients' EMR.) The data store 214 is further configured to store information, for instance, associated with a plurality of medical social network groups, for instance, medical condition support groups and the like. Such information may include, without limitation, demographic and medical information related to members of the medical social network group, archived group discussions, and the like. In embodiments, the data store 214 is configured to be searchable for one or more attributes and/or attribute values associated with a particular individual, medical social network groups, and attributes and/or attribute values associated with members of medical social network groups. It will be understood and appreciated by those of ordinary skill in the art that the information stored in the data store 214 may be configurable and may include any information relevant to patients' EMRs, patients' health records or other collections of medical data over which a subject patient has at least partial control of exposure, medical social network groups, and the like. The content and volume of such information are not intended to limit the scope of embodiments of the present invention in any way. Further, though illustrated as a single, independent component, the data store 214 may, in fact, be a plurality of data stores, for instance, a database cluster (e.g., database cluster 112 of FIG. 1), portions of which may reside on the server 210, the user device 212, another external computing device (not shown) and/or any combination thereof.

The server 210 includes various components and is configured to operate utilizing at least a portion of the information stored in the data store 214. The illustrated server 210 includes a user-submitted data receiving component 218, a health record extracting and deriving component 220, a user-anonymity degree calculating component 222 and a presentation component 224. It will be understood and appreciated by those of ordinary skill in the art that other components not shown may also be included with the system 200. Further, additional components not shown may also be included within any of the server 210, the user device 212, the data store 214, and/or another external computing device (not shown). Any and all such variations are contemplated to be within the scope of embodiments hereof.

The user-submitted data receiving component 218 is configured for receiving user-submitted data. Such user-submitted data may include, without limitation, user-attributes and/or associated attribute values, a general indication that a user desires to join a medical social network group, an indication that a user desires to join a particular medical social network group, an indication of a user's desire to expose one or more user-attributes and/or any attribute values associated therewith to the members of one or more medical social network groups, an indication of a user's desire to maintain privacy related to one or more user-attributes and/or any associated attribute values (i.e., an indication of a declination to expose such attributes/values), user-input questions and comments intended for presentation to the members of one or more medical social network groups, and the like.

As utilized herein, "user-attributes" are attributes of the subject user that are in some way related to user demographics, medical conditions, medical diagnoses, treatments, or the like. For instance, a user's gender, age, socio-economic status, city and/or state of residence, and the like may be user-attributes. Additionally, symptoms the user is experiencing or has experienced, whether or not directly tied to a particular diagnosis may be user-attributes, as may any clinical diagnosis the user has received. Still further, any medications, therapies, and the like that the user has been prescribed (or had recommended) for treatment of any clinical diagnosis, symptom, medical condition, or the like may be user-attributes, as may the identity of the subject user's clinician(s) and or visited clinical facilities. Any and all such attributes, and any combination thereof, as well as other attributes of a user not particularly delineated herein, are intended to be within the scope of the term "user-attributes."

User-attributes may have one or more attribute values associated therewith. For instance, a user's gender may be a user-attribute and either "male" or "female" may be an attribute value associated with the user-attribute "gender." Similarly, a user's state of residence may be a user-attribute and, for instance, "Missouri" may be an associated attribute value. In these exemplary instances, the user-attributes are associated with an ontology that includes a single-level. That is, the user-attributes are associated with a plurality of attribute values, each of which are independent of the others and have the same level of specificity as the others. In some instances, the plurality of attribute values may be binary, such as "yes" or "no." Some user-attributes are associated with multi-level ontologies, lending themselves to a plurality of attribute values being associated therewith, some of which have differing levels of specificity. For instance, for the user-attribute "age," there may be multiple hierarchical levels—each representing an increasing level of specificity (e.g., no age stated-middle-aged-45-55 years old-52 years old). Each hierarchical or ontological level in this instance is an attribute value associated with the user-attribute "age," and each has a different level of specificity relative to the others.

As more fully described below, user-attributes having multi-level ontologies related thereto permit differing degrees of anonymity depending upon which hierarchical level the user chooses to expose to other members of a medical social network group. For instance, in the above example, a user would have greater anonymity by indicating that he or she is middle-aged than if there was exposure to the user's age of 52. Similarly, a user would have a greater anonymity by indicating that he or she has heart disease than by exposing that he or she had NYHA Class III Heart Failure (the two attribute values being related by way of a multi-level ontology, e.g., heart disease-heart failure-moderate heart failure-NYHA Class III Heart Failure).

Returning now to FIG. 2, the health record extracting and deriving component 220 is configured to extract information (e.g., user-attributes and corresponding attribute values) from a user's health record or other collection of medical data over which the user has at least partial control of exposure and/or to derive information there from. For instance, a user may have an explicit entry in her health record indicating that her date of birth is Mar. 1, 1985. The health record extracting and deriving component is configured to mine the health record and extract the birth date (i.e., Mar. 1, 1985) and/or to derive the user's age from the data explicitly contained in the health record. As more fully described below, this extracted and/or derived data may then be utilized to provide calculated user-anonymity degrees to the user conditioned upon exposure of all or a subset of the extracted/derived data.

The health record extracting and deriving component 220 is further configured to extract and/or derive attribute values from health records, or other collections of medical data over which a subject patient has at least partial control of exposure, of each of a plurality of members of one or more medical social network groups, the group-member attribute values being capable of being utilized to calculate comparative degrees of user-anonymity, as more fully described below. In embodiments, the health record extracting and deriving component 220 mines the health record of one or more group members for any information contained therein. In other embodiments, the health record extracting and deriving component 220 mines only attribute values that the associated group member has elected to reveal to other members of the medical social network group. Any and all variations, and any combination thereof, are contemplated to be within the scope of embodiments of the present invention.

The user-anonymity degree calculating component 222 is configured to calculate a plurality of user-anonymity degrees, each conditioned upon exposure of all or a subset of all extracted, derived, and/or user-submitted attribute values. In this regard, the user-anonymity degree calculating component 222 utilizes attribute values associated with the user and compares them to attribute values for the same user-attributes associated with one or more members of a particular medical social network group. The user-anonymity degree calculating component 222 then utilizes statistical masking by a process of ontologic blurring to calculate a degree of user-anonymity, the calculated degree of user-anonymity being conditioned upon the user exposing the compared attribute value(s) to members of the medical social network group. Exemplary statistical masking techniques are known to those of ordinary skill in the art and include those used by the United States Census Bureau to mask zip code populations having too few persons living therein. Thus, the user-anonymity degree calculating component 222 is configured to receive user-submitted data from the user-submitted data receiving component 218, to receive data extracted and/or derived utilizing the health record extracting and deriving component 220, to access data associated with medical social network groups and their associated members (e.g., from data store 214), and to utilize the received and/or accessed data to calculate one or more user-anonymity degrees based thereon.

It should be noted that in many instances, user-anonymity is calculated based upon an aggregation of exposure of a plurality of user-attribute values. That is, if a user has twenty user attribute values associated with a particular collection of medical data and he or she chooses to mask fifteen of the values, the calculated degree of user-anonymity may be that there are 200 persons just like the user in a group of 5000 members, which would indicate a relatively high level of anonymity. If, however, the user chooses to mask only five of the values, the calculated degree of user-anonymity may be that there are only 3 persons just like the user in the group of 5000 members, which indicates that the user's true identity would be much easier to confirm.

The presentation component 224 is configured to cause at least one or more calculated degrees of user-anonymity to be presented to the user, for instance, displayed in association with a screen display of the user device 212. In embodiments, the presentation component 224 may be further configured to cause presentation of user-attributes and/or attribute values utilized to calculate degrees of user-anonymity, suggested medical social network groups, and the like. Various forms of presentation for the data are contemplated to be within the scope of embodiments hereof and are not intended to limit the present invention. For instance, degrees of user-anonymity may be displayed graphically, numerically, or any combination thereof.

Figure 3:
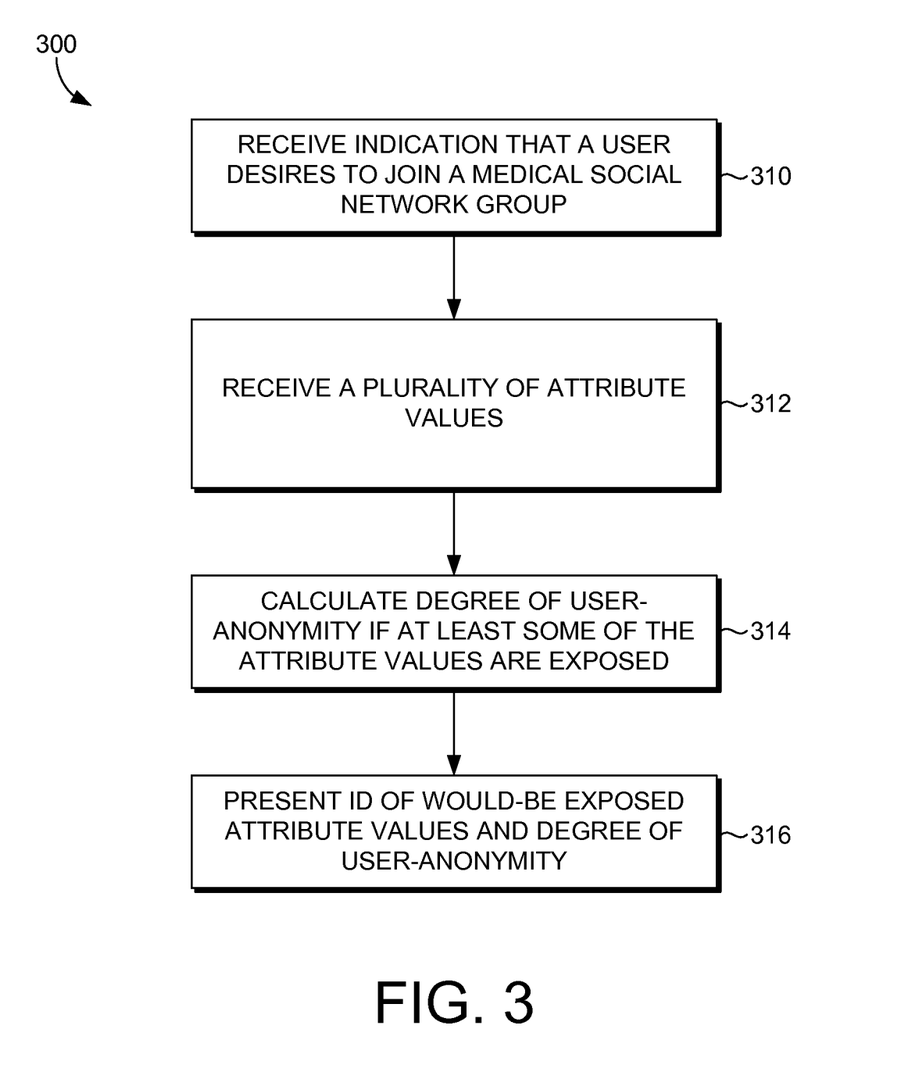
FIG. 3 is a flow diagram showing a method for using user-attribute ontologies to calculate user-anonymity degrees, in accordance with an embodiment of the present invention.

Turning now to FIG. 3, a flow diagram showing a method 300 for using ontologies to calculate user-anonymity degrees, in accordance with an embodiment of the present invention. As indicated at block 310, an indication is received that a user desires to join a medical social network group, the medical social network group having a plurality of members. The medical social network group may be, by way of example only, a condition support group, a medication information group, or the like. In embodiments, the indication that the user desires to join a medical social network group is received by the user-submitted data receiving component 218 of FIG. 2.

As indicated at block 312, a plurality of attribute values is received, for instance, utilizing one or more of user-submitted data receiving component 218 and health record extracting and deriving component 220 of FIG. 2. Each attribute value is associated with a user-attribute. In embodiments, each of a first and second of the plurality of attribute values is associated with a common user-attribute, and the common user-attribute includes a multi-level ontology related thereto. Further, each of the first and second attribute values is associated with a different level of the multi-level ontology. For instance, returning to an example described herein above, the attribute values of "professional" and "neurologist" may be received, each associated with the common user-attribute of "occupation," the two attribute values representing differing levels of specificity and being related to one another in a hierarchical fashion.

As indicated at block 314, at least one degree of user-anonymity is calculated, the calculated degree of user-anonymity being conditioned on exposure of at least one subset of the plurality of attribute values. In embodiments, the at least one degree of user-anonymity is calculated, for instance, by user-anonymity degree calculating component 222 of FIG. 2, using a statistical masking methodology. In this regard, the at least one degree of user-anonymity is calculated as it relates to attribute values for the same user-attributes but associated with other members of the medical social network group. In embodiments, the subset of the plurality of attribute values includes at least one of the first and second attribute values.

An indication of the calculated degree(s) of user-anonymity and an identity of each of the plurality of attribute values included in the at least one subset is presented, as indicated at block 316. The user may then utilize the presented information to determine whether exposure of the at least one subset of the plurality of attribute values is acceptable or desirable. In embodiments, a plurality of calculated degrees of user-anonymity is calculated and each is presented to the user to aid the user in determining the specificity with which he or she wishes to expose themselves to members of the medical social network group. In embodiments, the calculated degree(s) of user-anonymity and the identity of each of the attribute values included in the at least one subset are presented utilizing the presentation component 224 of FIG. 2.

Figure 4:
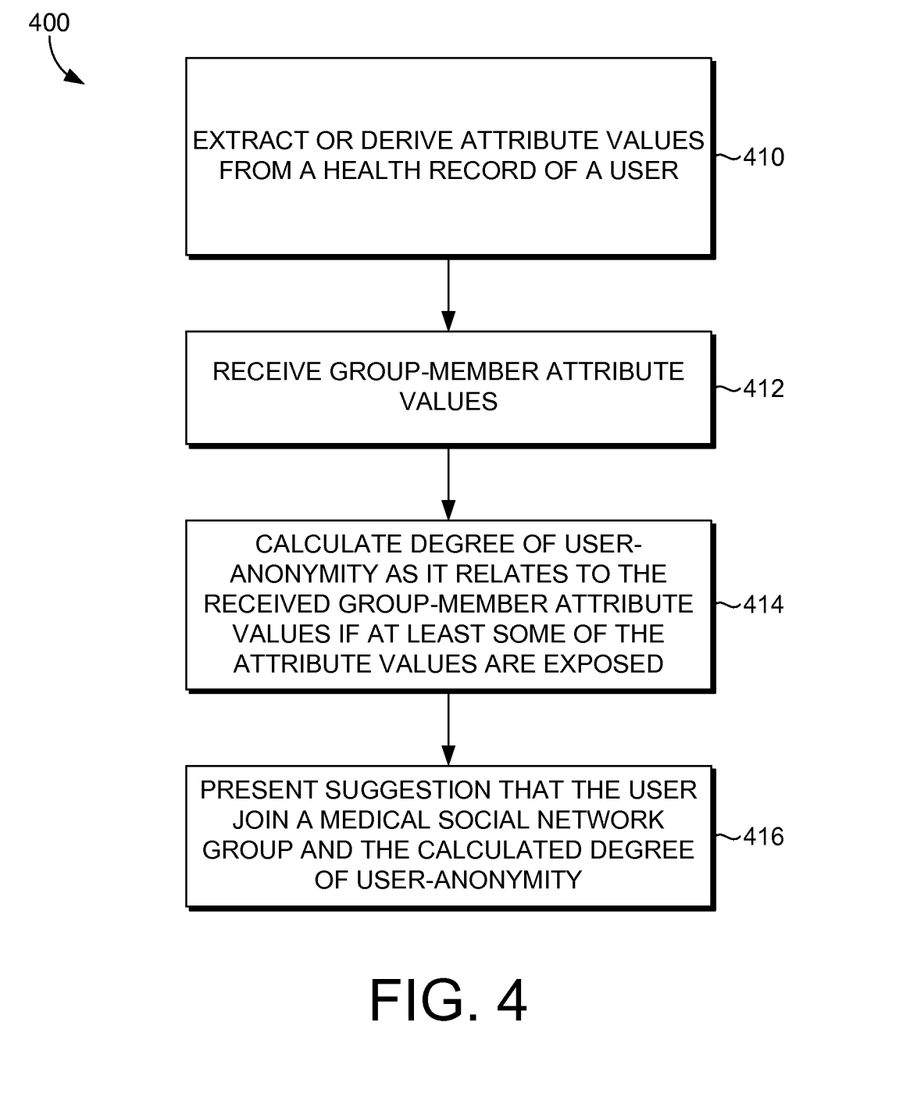
FIG. 4 is a flow diagram showing a method for providing medical social network group suggestions having anonymity degrees calculated, at least in part, using user-attribute ontologies, in accordance with an embodiment of the present invention.

With reference now to FIG. 4, a flow diagram is illustrated showing a method 400 for providing medical social network group suggestions having anonymity degrees calculated, at least in part, using user-attribute ontologies, in accordance with an embodiment of the present invention. As indicated at block 410, a plurality of attribute values is extracted from a health record of a user. Each attribute value is associated with a user-attribute. In embodiments, a first and a second of the plurality of attribute values are associated with a common user-attribute. In embodiments, the common user-attribute includes a multi-level user-attribute ontology related thereto and each of the first and second attribute values is associated with a different level of the multi-level user-attribute ontology. In embodiments, the plurality of attribute values is extracted utilizing the health record extracting and deriving component 220 of FIG. 2.

As indicated at block 412, group-member attribute values for a plurality of members of a medical social network group are received. In embodiments wherein the plurality of attribute values is associated with a common user-attribute having a multi-level ontology associated there with, the group-member attribute values are for at least the same levels of the multi-level user-attribute ontology associated with the common user-attribute. In embodiments, the group-member attribute values are received utilizing one or both of the user-submitted data receiving component 218 and the health record extracting and deriving component 220 of FIG. 2.

As indicated at block 414, at least one degree of user-anonymity is calculated as it relates to the received group-member attribute values, the degree of user-anonymity being conditioned on exposure of at least one subset of the plurality of attribute values. In embodiments, the subset contains at least one of the first and second of the plurality of attribute values. In embodiments, a plurality of degrees of user-anonymity is calculated, each degree of anonymity being conditioned on exposure of a different subset of the plurality of attribute values, at least a first of the different subsets containing the first of the plurality of attribute values and a second of the different subsets containing the second of the plurality of attribute values In embodiments, the user-anonymity degree(s) is calculated utilizing the user-anonymity degree calculating component 222 of FIG. 2.

A suggestion that the user join the medical social network group and the calculated degree(s) of user-anonymity is presented upon determining that the calculated degree of user-anonymity meets or exceeds a threshold degree of user-anonymity. This is indicated at block 416. The threshold degree of user-anonymity may be based upon a raw number (e.g., so long as at least X number of members of the medical social network group have the subset of attribute values in common, a suggestion that the user join the group is presented), a percentage (e.g., so long as at least X % of the group members have the subset of attribute values in common, a suggestion that the user join the group is presented), or any other indication of relative anonymity (or any combination thereof). In embodiments, the form of presentation is conditioned on the likelihood of revealing information that makes any one member of the medical social network group personally identifiable. In embodiments, the suggestion that the user join the medical social network group, and the calculated degree of user-anonymity, are presented utilizing the presentation component 224 of FIG. 2.

Figure 5:
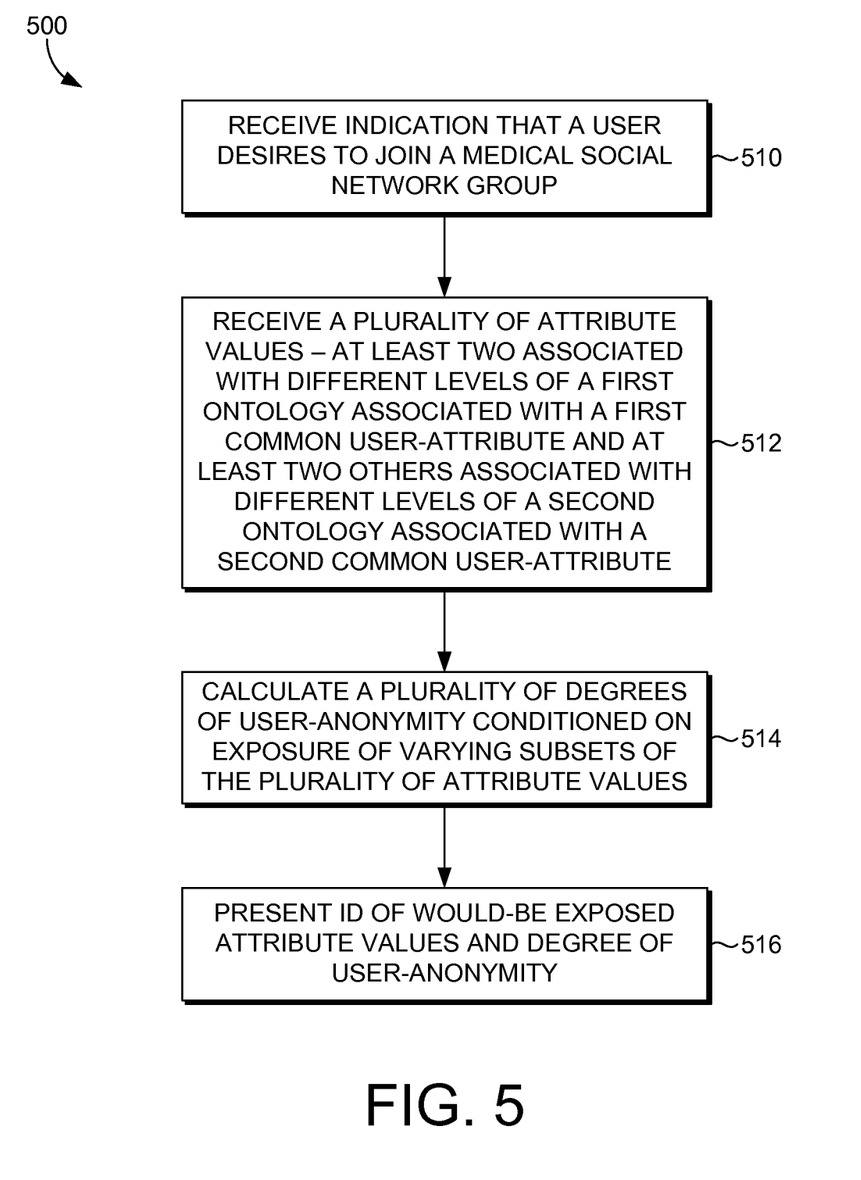
FIG. 5 is a flow diagram showing a method for using user-attribute ontologies to calculate user-anonymity degrees, in accordance with an embodiment of the present invention.

With reference to FIG. 5, a flow diagram is illustrated showing a method 500 for using user-attribute ontologies to calculate user-anonymity degrees, in accordance with an embodiment of the present invention. As indicated at block 510, an indication that a user desires to join a medical social network group having a plurality of members is received, for instance, utilizing user-submitted data receiving component 218 of FIG. 2.

As indicated at block 512, a plurality of attribute values is received, each attribute value being associated with a user-attribute. A first and a second of the plurality of attribute values are associated with a first common user-attribute, and the first common user-attribute includes a first multi-level user-attribute ontology related thereto. Each of the first and second of the plurality of attribute values is associated with a different level of the first multi-level user-attribute ontology. Further, a third and a fourth of the plurality of attribute values are associated with a second common user-attribute, the second common user-attribute including a second multi-level user-attribute ontology related thereto. Each of the third and fourth of the plurality of attribute values is associated with a different level of the second multi-level user-attribute ontology. In embodiments, the plurality of attribute values is received using one or more of the user-submitted data receiving component 218 and the PCHR extracting and deriving component 220 of FIG. 2.

As indicated at block 514, a plurality of degrees of user-anonymity is calculated, each of the plurality of user-anonymity degrees being conditioned on exposure of varying subsets of the plurality of attribute values. A first subset contains at least one of the first and second of the plurality of attribute values and one of the third and fourth of the plurality of attribute values. In embodiments, the degrees of user-anonymity are calculated utilizing user-anonymity degree calculating component 222 of FIG. 2. In embodiments, at least one of the plurality of degrees of user-anonymity is calculated using a statistical blurring methodology.

An indication of the calculated degrees of user-anonymity and an identity of each of the plurality of attribute values included in the associated subset is presented, for instance, utilizing presentation component 224 of FIG. 2. This is indicated at block 516.

As can be understood, embodiments of the present invention provide computerized methods and systems for using user-attributes having associated user-attribute ontologies to calculate degrees of user-anonymity that are conditioned on exposure of attribute values associated with various user-attributes to members of a medical social network group. Embodiments hereof utilize statistical blurring methodologies, and take advantage of ontologies associated with various user-attributes that are in some way related to user demographics, medical conditions, medical diagnoses, or the like, to calculate degrees of user-anonymity. Users may then utilize the calculated degrees of user-anonymity to aid them in deciding whether they wish to join a particular medical social network group and/or how much information they would like to expose to members of a particular medical social network group.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

What is claimed is:

1. One or more computer hardware storage media having computer-executable instructions embodied thereon for performing a method in a clinical computing environment for using user-attribute ontologies to calculate user-anonymity degrees, the method comprising:
   receiving an indication that a user desires to join a medical social network group having a plurality of members;
   receiving a plurality of attribute values, each attribute value being associated with a user-attribute, wherein the plurality of attribute values comprises attribute values associated with user submitted data and attribute values extracted from the user's electronic health records, wherein a first user-attribute value of the plurality of attribute values is a medical condition, wherein the first user-attribute value includes a multi-level user-attribute ontology related thereto;
   receiving group-member attribute values for the plurality of members of the medical social network group;
   calculating a degree of user-anonymity for the user conditioned on exposure of at least one subset of the plurality of attribute values to the medical social network group, wherein the calculated degree of user-anonymity is based at least in part on the group-member attribute values; and
   presenting an indication of the calculated degree of user-anonymity and an identity of each of the plurality of attribute values included in the at least one subset.

2. The one or more computer hardware storage media of claim 1,
   wherein a second user attribute value and the first user attribute value of the plurality of attribute values are associated with a common user-attribute,
   wherein each of the first and second of the plurality of attribute values is associated with a different level of the multi-level user attribute ontology,
   and wherein the at least one subset of the plurality of attribute values includes at least one of the first and second of the plurality of attribute values.

3. The one or more computer hardware storage media of claim 1, wherein at least a portion of the received group-member attribute values is derived or extracted from information an associated group member has elected to expose to other members of the medical social network group.

4. The one or more computer hardware storage media of claim 1, wherein at least a portion of the group-member attribute values is derived or extracted from a health record of an associated group member.

5. The one or more computer hardware storage media of claim 4, wherein at least a portion of the received group-member attribute values is derived or extracted from information the associated group member has elected to expose to other members of the medical social network group, and wherein the information comprises a subset of the group-member attribute values derived or extracted from the health record of the associated group member.

6. The one or more computer hardware storage media of claim 1, wherein calculating the degree of user-anonymity conditioned on exposure of at least one subset of the plurality of attribute values comprises calculating a plurality of varying degrees of user-anonymity, each of the plurality of varying degrees of user-anonymity being conditioned, at least in part, on exposure of a different subset of the plurality of attribute values, and wherein presenting the indication of the calculated degree of user-anonymity and the identity of each of the plurality of attribute values included in the at least one subset comprises presenting an indication of each of the plurality of varying degrees of user-anonymity and the identity of each of the plurality of attribute values included in each different subset of the plurality of attribute values.

7. The one or more computer hardware storage media of claim 1, wherein at least a portion of the plurality of attribute values is derived or extracted from information the user has elected to expose to other members of the medical social network group.

8. The one or more computer hardware storage media of claim 1, wherein at least a portion of the plurality of attribute values is derived or extracted from information the user has elected to expose to other members of the medical social network group, and wherein the information comprises a subset of the plurality of attribute values derived or extracted from the health record of the user.

9. A method in a clinical computing environment for providing medical social network group suggestions having anonymity degrees calculated, at least in part, using user-attribute ontologies, the method comprising the following computer-implemented steps:

extracting a plurality of attribute values from a health record of a user, each attribute value being associated with a user-attribute, wherein a first user-attribute value of the plurality of attribute values is a medical condition, wherein the first user-attribute value includes a multi-level user-attribute ontology related thereto;

receiving attribute values associated with user submitted data;

receiving group-member attribute values for a plurality of members of a medical social network group, the group-member attribute values being associated with a common user-attribute associated with the plurality of attribute values;

calculating a degree of user-anonymity for the user as it relates to the received group-member attribute values, the degree of user-anonymity being conditioned on exposure of at least one subset of the plurality of attribute values and at least a portion of the attribute values associated with user submitted data; and presenting a suggestion that the user join the medical social network group and the calculated degree of user-anonymity upon determining that the calculated degree of user-anonymity meets or exceeds a threshold degree of user-anonymity, wherein the threshold degree of user-anonymity is based on the group-member attribute values of the plurality of members in the medical social network group.

10. The method of claim 9, wherein a second user attribute value and the first user attribute value of the plurality of attribute values are associated with a common user-attribute, wherein each of the first and second of the plurality of attribute values is associated with a different level of the multi-level user-attribute ontology, and wherein the at least one subset of the plurality of attribute values includes at least one of the first and second of the plurality of attribute values.

11. The method of claim 10, wherein calculating the degree of user-anonymity comprises calculating a plurality of degrees of user-anonymity each conditioned on exposure of a different subset of the plurality of attribute values, at least a first of the different subsets containing the first of the plurality of attribute values and a second of the different subsets containing the second of the plurality of attribute values, and wherein presenting a suggestion that the user join the medical social network group and the calculated degree of user-anonymity upon determining that the calculated degree of user-anonymity meets or exceeds the threshold degree of user-anonymity comprises presenting the suggestion that the user join the medical social network group and each of the plurality of calculated degrees of user-anonymity upon determining that at least one of the plurality of calculated degrees of user-anonymity meets or exceeds the threshold degree of user-anonymity.

12. The method of claim 9, wherein calculating the degree of user-anonymity comprises calculating the degree of user-anonymity using a statistical masking methodology.

13. The method of claim 9, wherein at least a portion of the received group-member attribute values is derived or extracted from a health record of an associated group member.

14. The method of claim 13, wherein at least a portion of the received group-member attribute values is derived or extracted from a set of information the associated group member has elected to reveal to other members of the medical social network group, and wherein the set of information comprises a subset of the group-member attribute values derived or extracted from the health record of the associated group member.

15. The method of claim 9, wherein at least a portion of the received group-member attribute values is derived or extracted from a set of information an associated group member has elected to reveal to other members of the medical social network group.

16. One or more computer hardware storage media having computer-executable instructions embodied thereon for performing a method in a clinical computing environment for using user-attribute ontologies to calculate user-anonymity degrees, the method comprising:

receiving an indication that a user desires to join a medical social network group having a plurality of members;

receiving a plurality of attribute values, each attribute value being associated with a user-attribute, wherein a first and a second of the plurality of attribute values are associated with a first common user-attribute, wherein the first common user-attribute is a medical condition, wherein the first common user-attribute includes a first multi-level user-attribute ontology related thereto, and wherein each of the first and second of the plurality of attribute values is associated with a different level of the first multi-level user-attribute ontology, wherein a third and a fourth of the plurality of attribute values are associated with a second common user-attribute, wherein the second common user-attribute includes a second multi-level user-attribute ontology related thereto, and wherein each of the third and fourth of the plurality of attribute values is associated with a different level of the second multi-level user-attribute ontology, calculating a plurality of degrees of user-anonymity conditioned on exposure of different subsets of the plurality of attribute values, a first subset containing at least one of the first and second of the plurality of attribute values and one of the third and fourth of the plurality of attribute values; and presenting an indication of the calculated degrees of user-anonymity and an identity of each of the plurality of attribute values included in the associated subset.

17. The one or more computer hardware storage media of claim 16, wherein at least a portion of the plurality of attribute values is derived or extracted from a health record of the user.

18. The one or more computer hardware storage media of claim 16, wherein the method further comprises receiving group-member attribute values for a plurality of members of the medical social network group, and wherein calculating the plurality of degrees of user-anonymity comprises calculating each of the plurality of degrees of user-anonymity as it relates to the received group-member attribute values.

* * * * *